(12) United States Patent
Sasayama

(10) Patent No.: US 10,161,872 B2
(45) Date of Patent: Dec. 25, 2018

(54) OPTICAL MEASURING DEVICE AND SAFETY DEVICE USED THEREIN

(71) Applicant: SHIMADZU CORPORATION, Kyoto-shi, Kyoto (JP)

(72) Inventor: Tomoki Sasayama, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/098,598

(22) Filed: Apr. 14, 2016

(65) Prior Publication Data

US 2017/0299515 A1    Oct. 19, 2017

(51) Int. Cl.
  *G01N 21/64* (2006.01)
  *G02B 5/20* (2006.01)

(52) U.S. Cl.
  CPC ......... *G01N 21/645* (2013.01); *G02B 5/208* (2013.01); *G01N 2021/6463* (2013.01); *G01N 2201/022* (2013.01); *G01N 2201/025* (2013.01)

(58) Field of Classification Search
  CPC ........... G01N 21/645; G01N 2201/022; G01N 2201/025; G01N 2021/6463; G01N 2201/02; G02B 5/208; G01J 3/10; G01J 3/0291; G01J 2003/1213; G01J 3/0232; G01J 1/0437; G01J 5/04; G01J 3/0213; G01J 5/0831; G01J 1/044; G01J 5/0834
  See application file for complete search history.

(56) References Cited

U.S. PATENT DOCUMENTS

| | | | | |
|---|---|---|---|---|
| 3,626,929 A | * | 12/1971 | Sanz | A61B 5/150022 600/583 |
| 4,213,703 A | * | 7/1980 | Haunold | G01N 21/0332 250/361 C |
| 5,108,175 A | * | 4/1992 | Whitlock | G01N 21/76 250/239 |
| 5,139,745 A | * | 8/1992 | Barr | G01N 21/76 250/361 C |
| 5,684,582 A | * | 11/1997 | Eastman | G01J 3/02 356/328 |
| 6,549,275 B1 | * | 4/2003 | Cabuz | G01N 15/1456 356/39 |

(Continued)

FOREIGN PATENT DOCUMENTS

JP    2004-245979 A    9/2004

OTHER PUBLICATIONS http://www.thefreedictionary.com/portion.*

*Primary Examiner* — Mohamed K Amara
(74) *Attorney, Agent, or Firm* — Sughrue Mion, PLLC

(57) ABSTRACT

An optical measuring device including a sample placement portion for a measurement sample to be placed therein; a light source portion for emitting a measurement beam toward the measurement sample that is placed in the sample placement portion; and a detector for detecting sample information from a measurement sample that is disposed in the sample placement portion; a cover portion that is able to open and close, for accessing the interior of the sample placement portion, is formed on the sample placement portion; an optical element member for not transmitting light of at least a prescribed wavelength band within the measurement beam; and a driving mechanism that is linked mechanically with the opening and closing of the cover portion to move the optical element member.

3 Claims, 4 Drawing Sheets

(56) References Cited

U.S. PATENT DOCUMENTS

| | | | | |
|---|---|---|---|---|
| 6,809,826 B2* | 10/2004 | Robertson | ............... | B82Y 15/00 |
| | | | | 356/246 |
| 6,897,069 B1* | 5/2005 | Jarvis | ..................... | C12M 35/02 |
| | | | | 435/285.2 |
| 7,397,036 B2* | 7/2008 | Robertson | ............ | G01N 21/645 |
| | | | | 250/364 |
| 7,623,225 B2* | 11/2009 | Robertson, Jr. | ........... | G01J 3/02 |
| | | | | 356/213 |
| 8,189,199 B2* | 5/2012 | Robertson, Jr. | ........... | G01J 3/02 |
| | | | | 356/246 |
| 8,646,344 B2* | 2/2014 | Israelachvili | ............ | G01N 3/04 |
| | | | | 73/864.91 |
| 8,730,466 B2* | 5/2014 | Ashmead | ............... | G01J 3/0218 |
| | | | | 356/244 |
| D739,771 S * | 9/2015 | Jablonski | ............... | G01J 3/0291 |
| | | | | D10/81 |
| 9,869,636 B2* | 1/2018 | Mander | .................. | G01N 21/01 |
| 2003/0143752 A1* | 7/2003 | Feldsine | ................. | G01N 21/76 |
| | | | | 436/164 |
| 2010/0195098 A1* | 8/2010 | Zuo | ...................... | G01N 21/255 |
| | | | | 356/319 |
| 2012/0206714 A1* | 8/2012 | Higgins | ................. | G01J 3/0232 |
| | | | | 356/51 |
| 2012/0295249 A1* | 11/2012 | Cherubini | ............ | G01N 21/645 |
| | | | | 435/5 |
| 2013/0293976 A1* | 11/2013 | Takada | .................... | G03B 11/00 |
| | | | | 359/889 |
| 2014/0106470 A1* | 4/2014 | Kopacka | .............. | G01N 21/645 |
| | | | | 436/501 |
| 2015/0233760 A1* | 8/2015 | Kielhorn | ............... | G01J 3/0218 |
| | | | | 356/326 |
| 2016/0286197 A1* | 9/2016 | Schwarz | ............ | A61B 1/00096 |

* cited by examiner (a) PRIOR ART (b) PRIOR ART

OPTICAL MEASURING DEVICE AND SAFETY DEVICE USED THEREIN

TECHNICAL FIELD

The present invention relates to an optical measuring device for illuminating a sample with light from a light source and detecting transmitted light, reflected light, fluorescent light, or the like, using a photodetector, and relates to a safety device used therein.

BACKGROUND ART

Optical measuring devices have been implemented that illuminate a sample surface with a measurement beam and that detect light that is emitted from substances included in the sample. For example, a fluorescent light measuring device that is an example of an optical measuring device illuminates a sample surface with an excitation beam (a measuring beam) in a specific wavelength band. The excitation beam produces fluorescent light (sample information) that is unique to an element (a fluorescent substance) that is included in the substance surface, at an analysis position on the sample surface that is irradiated by the excitation beam, and this fluorescent light is detected and imaged to carry out identification and quantification of elements that exist in the analysis position on the sample surface (referencing, for example, Japanese Unexamined Patent Application Publication 2004-245979.

FIG. 4 is a schematic structural diagram illustrating the structure of a fluorescent light measuring device. Note that FIG. 4 (a) is a cross-sectional view illustrating the state wherein the measurement sample is measured, and FIG. 4 (b) is a cross-sectional view illustrating the state wherein the measurement sample is switched. Note that one direction that is horizontal with the earth is defined as the X direction; a direction that is perpendicular to the X direction and that is horizontal with the surface of the earth is defined as the Y direction; and the direction that is perpendicular to both the X direction and the Y direction is defined as the Z direction. The fluorescent light measuring device 101 comprises: a box-shaped sample placement portion 10 and having a measurement S disposed therein; a box-shaped device case 150 having a light source portion 20 and a photodetector 30 disposed therein; and a controlling portion (computer) 160 for controlling the fluorescent light measuring device 101 overall.

The sample placement portion 10 comprises a square base plate 11 and a cover portion 12, which has a square top face and sidewalls of a square cylindrical shape extending downward from the peripheral edge portions of the top face. An opening 11a is formed in a center portion of the base plate 11. The cover portion 12 is of a top-hinged type that is attached, to the base plate 11, so that the top face of one of the side walls is able to revolve, relative to the base plate 11, with the Y direction as the axis of revolution, as an axis of revolution 12a. In such a sample placement portion 10, the cover portion 12 can be opened to enable placement of a measurement S so that the analysis surface of the measurement S will block the opening 11a, and the cover portion 12 can be closed after placement of the measurement sample S, so that no outside light will be incident into the sample placement portion 10.

The device case 150 has a square bottom face and sidewalls of an essentially square cylindrical shape that are disposed extending upward from the peripheral edge portions of the square bottom face, where a base plate 11 is attached, and the axis of revolution 12a of the cover portion 12 is attached, to an upper portion of the device case 150. The light source portion 20 emits the excitation beam L of a specific wavelength band, and is disposed within the device case 150, so that an excitation beam L that is emitted is incident, from the Z direction, into the opening 11a through a half-mirror 25, or the like. As a result, by placing the analysis surface of the measurement S so as to block the opening 11a, the bottom face (the analysis surface) of the measurement S will be irradiated by the excitation beam L from the Z direction.

The photodetector 30 is that which detects the intensity of the fluorescent light, and is disposed within the device case 150, where the fluorescent light passes through the half-mirror 25, and the like, so as to be incident thereon. Consequently, when the analysis surface of the measurement S is irradiated by the excitation beam L, fluorescent light is produced at the analysis surface of the measurement sample S, and the intensity of the fluorescent light is detected by the photodetector 30.

The controlling portion 160 is disposed within the device case 150. When the functions carried out by the controlling portion 160 are divided into blocks and explained, there is a light source portion controlling circuit (not shown) for turning ON/OFF the power supply the light source portion 20 based on an input signal from the inputting portion 51, and a sample information acquisition controlling circuit (not shown) for acquiring, from the photodetector 30, the intensity of the fluorescent light.

In such a fluorescent light measuring device 101, the operator opens the cover portion 12 in order to switch the measurement sample S, but when ultraviolet radiation is used as the excitation beam L, there is the possibility that the operator will be exposed to the ultraviolet radiation when the cover portion 12 is opened, which is undesirable optically and thermally. Consequently, as a safety device for a case wherein the operator has forgotten to turn OFF the power supply, using an inputting portion 51, a tab portion 12b of a rod shape is formed on the cover portion 12, and a microswitch 140, to be pressed by the tab portion 12b, is disposed in the device case 150. Through this, when the cover portion 12 is closed, the tab portion 12b presses the microswitch 140 and a signal indicating that the microswitch is in the ON state is inputted into the controlling portion 160 from the microswitch 140, and the controlling portion 160 outputs, to the light source portion 20, a signal that enables the power supply of the light source to be turned ON. On the other hand, when the cover portion 12 is opened, the tab portion 12b ceases to press the microswitch 140, and thus the signal indicating the microswitch ON state is not inputted from the microswitch 140 into the controlling portion 160, and thus the controlling portion 160 outputs a signal that prevents the power supply of the light source from being turned ON. That is, the controlling portion 160 has a circuit for turning the power supply of the light source portion 20 ON/OFF based on the input signal from the microswitch 140.

SUMMARY OF THE INVENTION

Problem Solved by the Present Invention

However, in the fluorescent light measuring device 101 as described above, if there were a fault in the microswitch 140, then the signal indicating the microswitch ON state might not be inputted from the microswitch 140 into the controlling portion 160, and, as a result, the operator could be exposed to ultraviolet radiation when the cover portion 12 is opened. Moreover, if there were a fault in the controlling portion 160 for evaluating the signal from the microswitch 140, then, in this case as well, the signal that prevents the power supply of the light source from being turned ON might cease to be outputted, so the operator could be exposed to ultraviolet radiation when the cover portion 12 is opened. That is, faults may exist not only in the microswitch 140, but also through problems in circuits or logic calculating portions, such as the controlling portion 160. Given this, the object of the present invention is to provide an optical measuring enabling a high level of prevention of exposure of the operator to light, and to provide a safety device used therein.

Means for Solving the Problem

The optical measuring device according to the present invention, created in order to solve the problem set forth above, is an optical measuring device comprising: a sample placement portion for a measurement sample to be placed therein; a light source portion for emitting a measurement beam toward the measurement sample that is placed in the sample placement portion; and a detector for detecting sample information from a measurement sample that is disposed in the sample placement portion, wherein: a cover portion that is able to open and close, for accessing the interior of the sample placement portion, is formed on the sample placement portion; comprising: an optical element member for not transmitting light of at least a prescribed wavelength band within the measurement beam; and a driving mechanism that is linked mechanically with the opening and closing of the cover portion to move the optical element member, wherein, when the cover portion is opened, the driving mechanism places the optical element member in the light path from the light source portion to the measurement sample, and when the cover portion is closed, the driving mechanism places the optical element member outside of the light path from the light source portion to the measurement sample.

Here the "linked mechanically with the opening and closing of the cover portion" refers to being operated through a mechanical property, without an evaluation by the controlling portion, or the like, and may be, for example, a driving mechanism that uses a lever, a wire, or the like.

Effects of the Invention

As described above, given the optical measuring device according to the present invention, a driving mechanism is provided for moving the optical element member, mechanically linked to the opening and closing of the cover portion, and is thus able to eliminate the possibility of a problem with circuitry, a logic calculating portion, or the like, thereby making it possible to prevent, to a high level, the exposure of the operator to light.

Other Means for Solving the Problem, and Effects thereof

Moreover, in the invention set forth above, the optical element member can revolve with one end portion as the axis of revolution, and the driving mechanism is provided with a lever and a wire that connects one end portion of the lever with the optical element member, where the other end portion of the lever is pressed by the cover portion when the cover portion is closed, and not pressed by the cover portion when the cover portion is opened.

Additionally, the sample placement portion in the invention described above may be provided with a base plate that has an opening portion, and a cover portion that is able to open and close the top face of the base plate, wherein the measurement sample is placed on the top face of the base plate so as to block the opening portion.

Moreover, the safety device according to the present invention is a safety device used in an optical measuring device, comprising: a sample placement portion for a measurement sample to be placed therein; a light source portion for emitting a measurement beam toward a measurement sample that is placed in the sample placement portion; and a detector for detecting sample information from a measurement sample placed in the sample placement portion, wherein: an optical element member for not transmitting light of at least a prescribed wavelength band within the measurement beam; and a driving mechanism for linking mechanically to the opening and closing of the cover portion, to move the optical element member, wherein: the driving mechanism places the optical element member into the light path from the light source portion to the measurement sample when the cover portion is opened and places the optical element member outside of the light path from the light source portion to the measurement sample when the cover portion is closed.

BRIEF DESCRIPTIONS OF THE DRAWINGS

FORMS FOR CARRYING OUT THE INVENTION

Embodiments of the present invention will be explained below, using the figures. Note that the present invention is not limited to embodiments as explained below, but rather the present invention includes, of course, a variety of forms within a range that does not deviate from the spirit and intent thereof.

Figure 1:
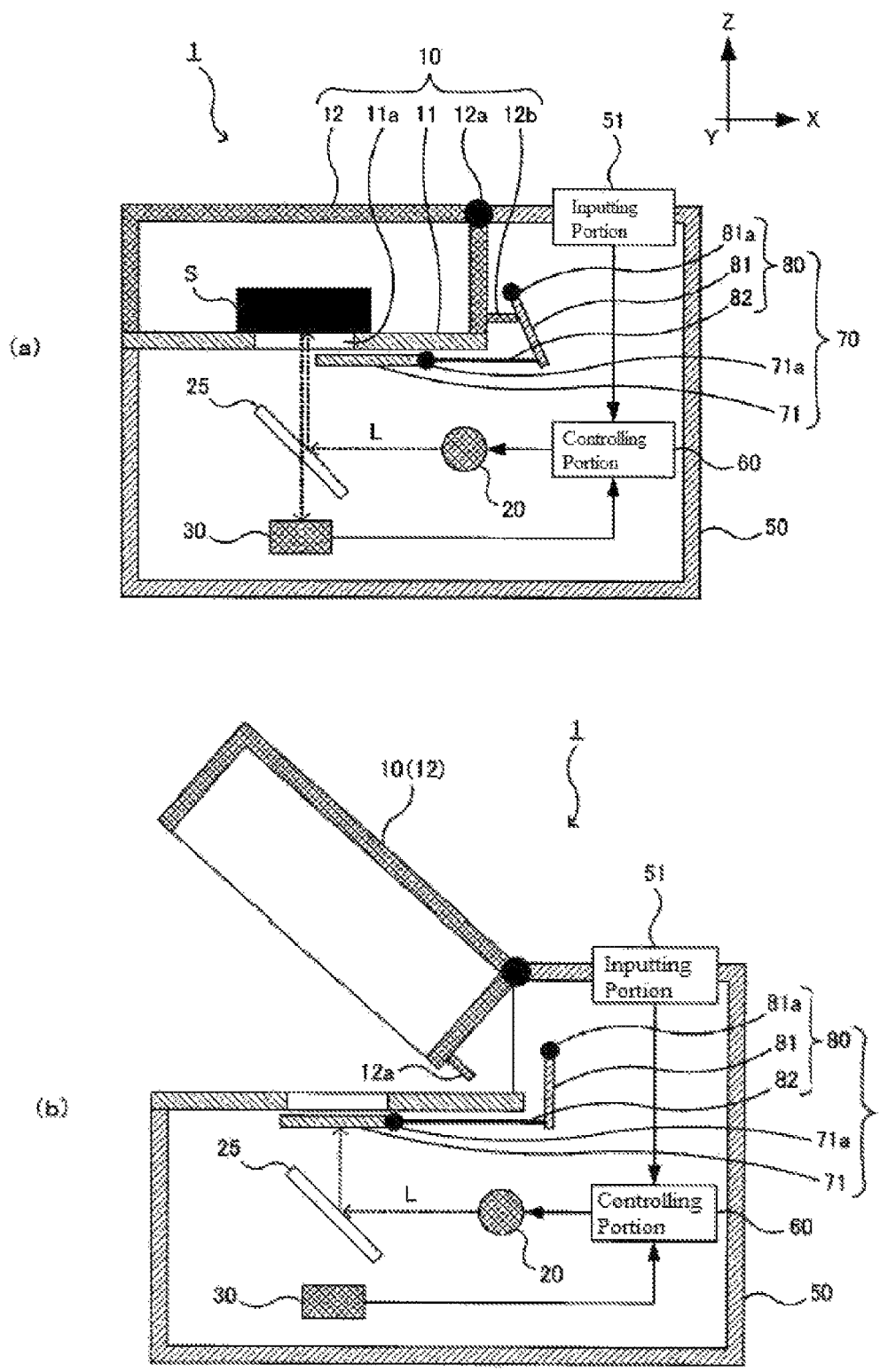
FIG. 1 is a schematic structural diagram illustrating an example of a fluorescent light measuring device according to an embodiment according to the present invention.

FIG. 1 is a schematic structural diagram illustrating an example of a fluorescent light measuring device according to an embodiment according to the present invention. Note that FIG. 1 (*a*) is a cross-sectional view illustrating the state when measuring the measurement sample, and FIG. 1 (*b*) is a cross-sectional view illustrating the state when switching the measurement sample. Moreover, identical reference symbols are applied to those parts that are similar to those of the fluorescent light measuring device 101. The fluorescent light measuring device 1 comprises: a box-shaped sample placement portion 10 for placement of the measurement S therein; a box-shaped device case 50 having a light source portion 20 and a detector 30 disposed therein; a safety device 70; and a controlling portion (a computer) 60 for carrying out overall control of the fluorescent light measuring device 1.

The sample placement portion 10 is provided with a square base plate 11 and a cover portion 12 having a square top face and having sidewalls of a square cylindrical shape extending downward from the peripheral edge portions of the top face. An opening 11a is formed in the center portion of the base plate 11. The cover portion 12 is of a top-hinged type that is attached so as to be able to revolve, relative to the base plate 11, with the Y direction as the axis of revolution, with the top face of one sidewall as the axis of revolution 12a. Given this sample placement portion 10, the cover portion 12 can be opened to enable the measurement S to be placed so that the analysis surface of the measurement S blocks the opening 11a, and, after the measurement S has been placed, the cover portion 12 can be closed so as to prevent outside light from being incident into the sample placement portion 10.

Figure 4:
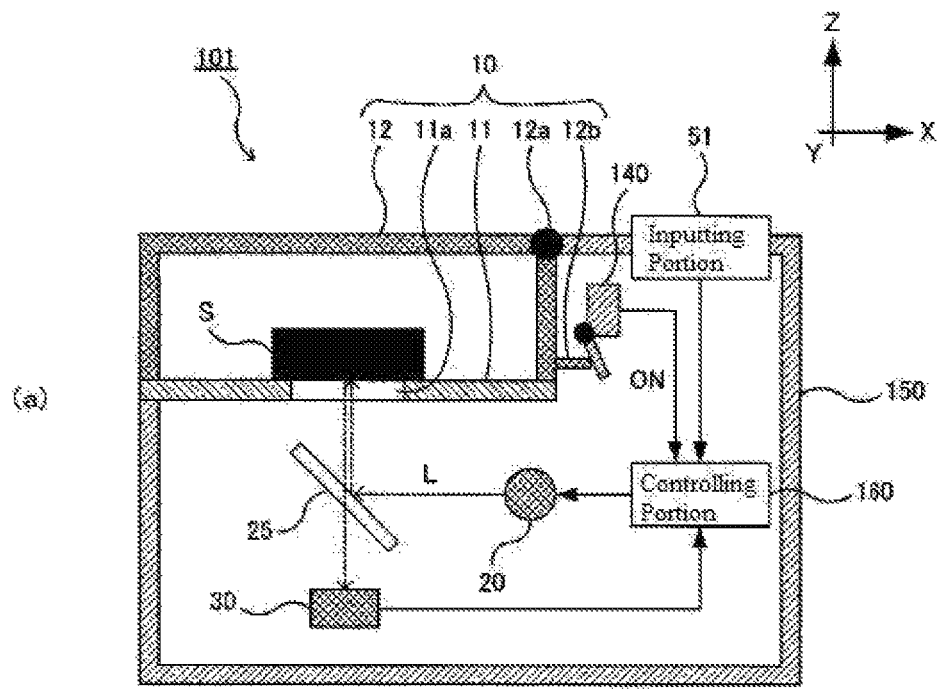
FIG. 4 is a schematic structural diagram of a conventional fluorescent light measuring device.
Figure 4:
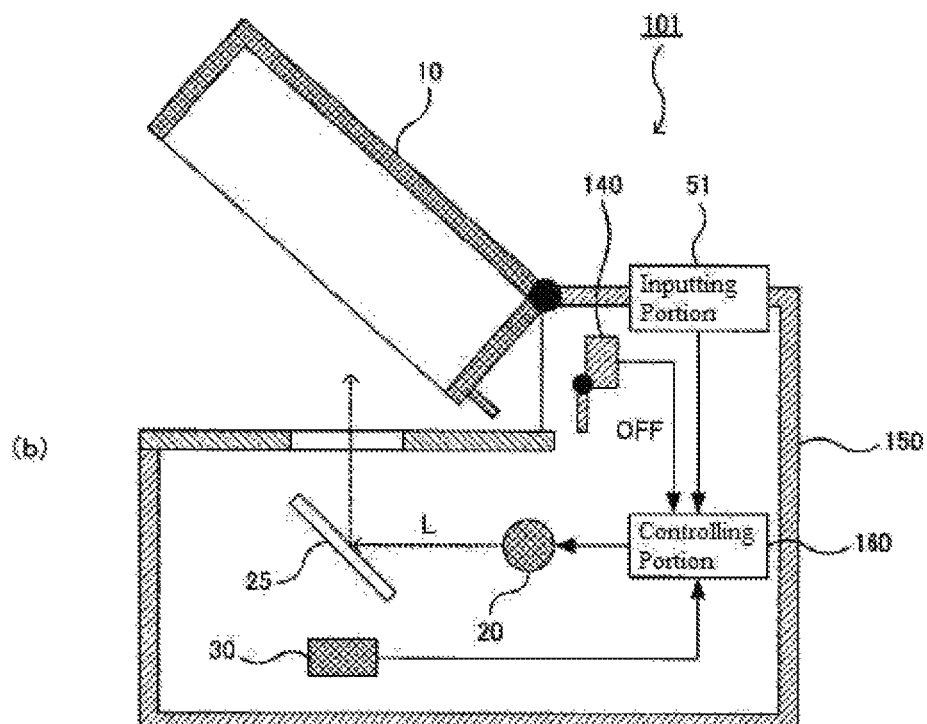

Moreover, on a lower portion of one sidewall of the cover portion 12, a tab portion 12b of a bar shape is formed protruding in the X direction. Note that in the fluorescent light measuring device according to the present invention, the tab portion 12b is not that which presses a microswitch 140 (referencing FIG. 4), but rather moves an end portion of a lever 81, of a bar shape, described below, in the X direction.

The device case 50 has a square bottom face and sidewalls that are essentially a square cylindrical shape, extending upward from the peripheral edge portions of the square bottom face, where a base plate 11 is attached, and an axis of revolution 12a of the cover portion 12 and an axis of revolution 81a of the lever 81 are attached, to an upper portion of the device case 50.

Figure 2:
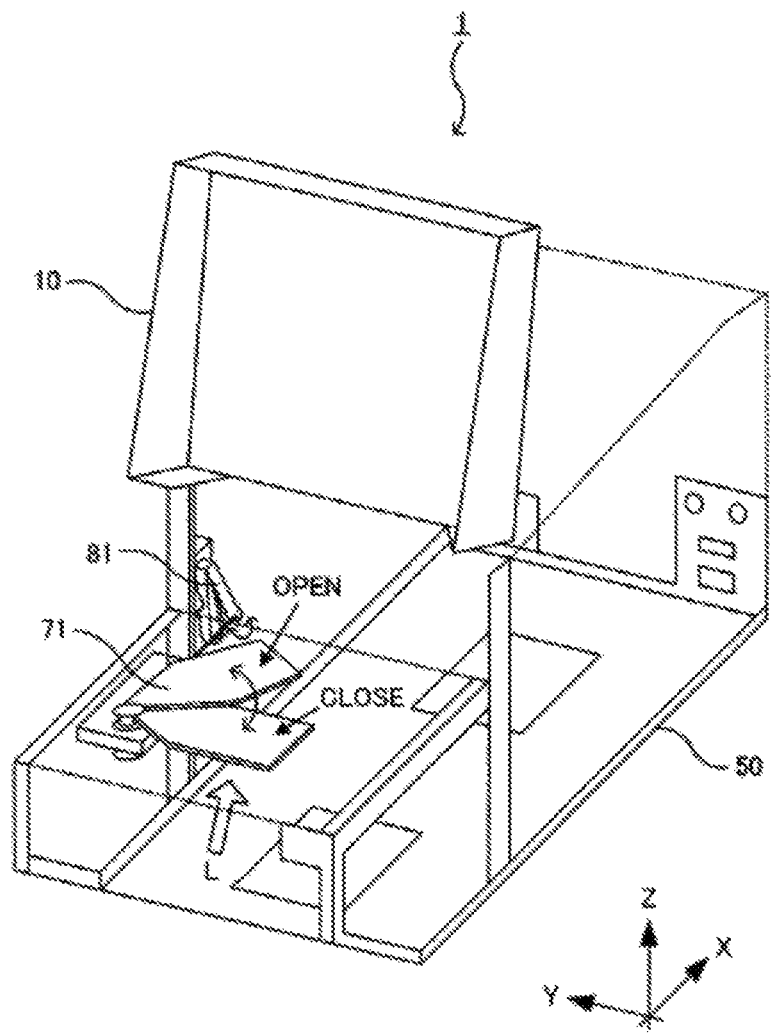
FIG. 2 is a perspective diagram for explaining the movement of the shutter.
Figure 3:
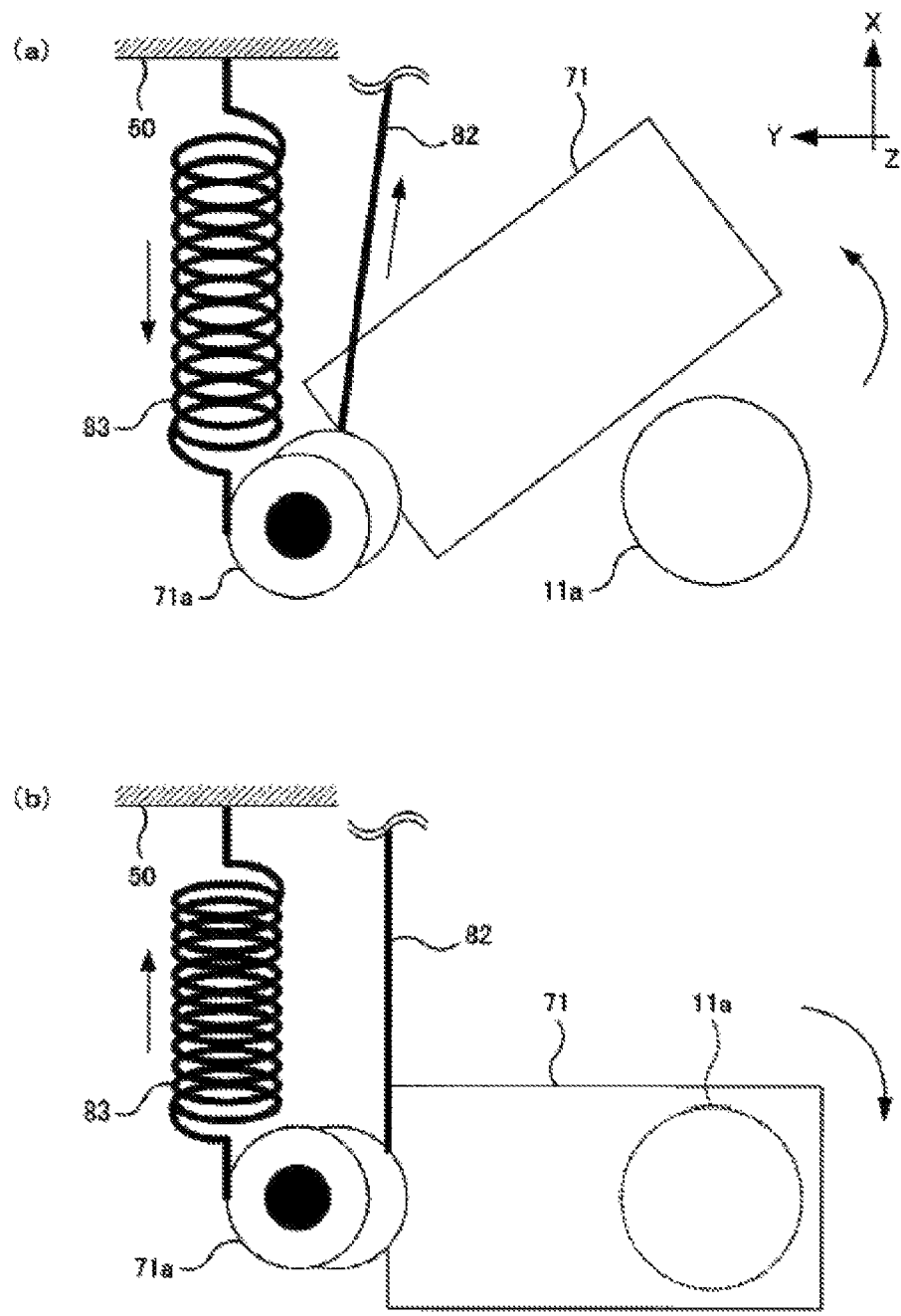
FIG. 3 is a plan view of critical portions for explaining the movement of the shutter.

The safety device 70 comprises a shutter (an optical element member) 71 and a driving mechanism 80 for moving the shutter 71. FIG. 2 is a perspective diagram for explaining the movement of the shutter 71, while FIG. 3 is a plan view illustrating the structure of critical portions in movement of the shutter 71. Moreover, FIG. 3 (a) shows a state wherein the measurement sample is measured, and FIG. 3 (b) shows a state wherein the measurement sample is switched. The shutter 71 is a plate-shaped body of an essentially square shape that is larger than the opening 11a, formed from a material through which the excitation beam L cannot pass. Moreover, the shutter 71 is disposed in parallel to the XY plane, and can move within the XY plane, with one end portion (a revolving portion) 71a as the axis of revolution. In this case, the shutter 71 may revolve so as to be disposed in a closed position, within the light path from the light source portion 20 to the opening 11a, or disposed in the open position, outside of the light path from the light source position 20 to the opening 11a. Through this, when the shutter 71 is placed in the closed position, the excitation beam L from the light source portion 20 will not arrive at the opening 11a (referencing FIG. 1 (b) and FIG. 3 (b)), while, on the other hand, when the shutter 71 is placed in the open position, the excitation beam L from the light source portion 20 will arrive at the opening 11a (referencing FIG. 1 (a) and FIG. 3 (a)).

The driving mechanism 80 comprises a lever 81, a wire 82, and a spring 83. The lever 81 is a plate-shaped body with an essentially square shape, and is disposed in parallel to the YZ plane, and is able to move with one end portion 81a as the axis of revolution. In this case, when the cover portion 12 is opened, the tab portion 12a will not contact the other end portion of the lever 81 (referencing FIG. 1 (b)), and when the cover portion 12 is closed, the tab portion 12a will press the other end portion of the lever 81 (referencing FIG. 1 (a)), so that the other end portion of the lever 81 will move a prescribed distance in the X direction.

The wire 82 connects the other end portion of the lever 81 and one end side of the revolving portion 71a of the shutter 71 in essentially the X direction. Moreover, the spring 83 connects the other end side of the revolving portion 71a of the shutter 71 to the device case 50, and acts so as to pull the other end side of the revolving portion 71a of the shutter 71 in the X direction. Through this, when the wire 82 pulls the one end side of the revolving portion 71a of the shutter 71 in essentially the X direction, the revolving portion 71a of the shutter 71 will revolve in the counterclockwise direction against the elastic force of the spring 83 (against the torque), where, on the other hand, if the wire 82 does not pull the one end side of the revolving portion 71a of the shutter 71 in essentially the X direction, then the revolving portion 71a of the shutter 71 will be revolved in the clockwise direction by the elastic force of the spring 83.

Given such a fluorescent light measuring device 1, if the operator forgets to use the inputting portion 51 to turn OFF the power supply, then when the cover portion 12 is opened, the tab portion 12a will stop pressing the other end portion of the lever 81, so that the wire 82 will not pull the one inside of the revolving portion 71a of the shutter 71 in essentially the X direction, and thus the revolving portion 71a of the shutter 71 will be revolved in the clockwise direction by the elastic force of the spring 83. The result is that the shutter 71 is placed into the closed position, that is, is inserted into the light path from the light source portion 20 to the opening 11a, so that the excitation beam L from the light source portion 20 will not arrive at the opening 11a.

On the other hand, when the operator closes the cover portion 12, the other end portion of the lever 81 is pressed by the tab portion 12a, so that the wire 82 pulls the one end side of the revolving portion 71a of the shutter 71 in essentially the X direction, to revolve the revolving portion 71a of the shutter 71 in the counterclockwise direction. The result is that the shutter 71 is placed into the open position, that is, is withdrawn from within the light path from the light source portion 20 to the opening 11a, so that the excitation beam from the light source portion 20 will arrive at the opening 11a.

Moreover, the controlling portion 60 is disposed within the device case 50, where, when the functions carried out by the controlling portion 60 are divided into blocks for explanation, the controlling portion 60 has a light source portion controlling circuit (not shown) for turning the power supply for the light source portion 20 ON and OFF based on an input signal from the inputting portion 51, and a sample information acquisition controlling circuit (not shown) for acquiring, from the photodetector 30, the intensity of the fluorescent light. Note that the fluorescent light measuring device 1 according to the present invention may be provided with a microswitch 140 (referencing FIG. 4) and a circuit for turning the power supply of the light source portion 20 ON/OFF based on an input signal from the microswitch 140.

As described above, the fluorescent light measuring device 1 according to the present invention is provided with a driving mechanism 80 that is linked mechanically to the opening and closing of the cover portion 12 so as to move the shutter 71, thus enabling the elimination of the possibility of problems with circuitry or logic calculating portions, or the like, thus enabling a high level of prevention of exposure of the operator to the excitation beam L.

<Other Embodiments>

(1) While in the fluorescent light measuring device 1 described above, the structure was one wherein the shutter 71 was formed from a material that does not transmit the excitation beam L, the structure may instead be one that uses a filter formed from a material that transmits visible light and does not transmit the excitation beam of a prescribed wavelength band. If, in such a fluorescent light measuring device, a visible light camera were built in, then it would be possible to observe an imaging result using visible light even when the cover portion is open, making it possible to move the measurement sample to the appropriate position.

(2) While the fluorescent light measuring device 1 described above was structured with the driving mechanism 80 comprising a lever 81, a wire 82, and a spring 83, so that the shutter 71 is moved by the driving mechanism 80, the present invention is not limited to only these means. It may be structured through other means insofar as a mechanism is provided wherein the shutter is linked mechanically to the movement of the cover portion so that when the cover portion is in the open state, that is, when in a state wherein the operator is able to access the measurement sample, the shutter is inserted into the light path from the light source portion to the excitation beam, and when the cover portion is in the closed state, that is, when in a state wherein the operator is unable to access the measurement sample, the shutter is withdrawn from the light path of the excitation beam

INDUSTRIAL APPLICABILITY

The present invention can be used in optical measuring devices, and the like, wherein samples are irradiated with light from a light source and transmitted light, reflected light, fluorescent light, or the like, therefrom is detected by a photodetector.

EXPLANATION of REFERENCE SYMBOLS

1: Fluorescent Light Measuring Device (Optical Measuring Device)
10: Sample Placement Portion
12: Cover Portion
20: Light Source Portion
30: Detector
71: Shutter (Optical Element Member)
80: Driving Mechanism

What is claimed:
1. An optical measuring device comprising:
a sample placement portion comprising a base plate and a cover portion that can be opened and closed in order to access an interior of the sample placement portion and is capable of covering an upper surface of the base plate on which a measurement sample is placed, the base plate having an aperture portion that is occluded by the measurement sample;
a light source portion which emits a measurement beam toward the measurement sample that is placed in the sample placement portion;
a detector which detects sample information from the measurement sample placed in the sample placement portion;
a shutter which does not transmit light of at least a prescribed wavelength band within the measurement beam; and
a driving mechanism for linking mechanically to an opening and closing of the cover portion, to move the shutter,
wherein: the driving mechanism places the shutter into a light path from the light source portion to the sample placement portion so as to occlude the aperture portion when the cover portion is opened and places the shutter outside of the light path from the light source portion to the sample placement portion so as to not occlude the aperture portion when the cover portion is closed,
wherein the cover portion can be opened so as to access the measurement sample.
2. The optical measuring device as set forth in claim 1, wherein:
the shutter is configured to revolve with one end portion thereof as an axis of revolution;
the driving mechanism comprises a lever and a wire that connects one end portion of the lever and the shutter; and
the other end portion of the lever is pressed by the cover portion when the cover portion is closed, and not pressed by the cover portion when the cover portion is opened.
3. A safety device used in an optical measuring device, comprising:
a sample placement portion comprising a base plate and a cover portion that can be opened and closed in order to access an interior of the sample placement portion and is capable of covering an upper surface of the base plate on which a measurement sample is placed, the base plate having an aperture portion that is occluded by the measurement sample;
a light source portion which emits a measurement beam toward the measurement sample that is placed in the sample placement portion;
a detector which detects sample information from the measurement sample placed in the sample placement portion;
a shutter which does not transmit light of at least a prescribed wavelength band within the measurement beam; and
a driving mechanism for linking mechanically to an opening and closing of the cover portion, to move the shutter,
wherein: the driving mechanism places the shutter into a light path from
the light source portion to the sample placement portion so as to occlude the aperture portion when the cover portion is opened and places the shutter outside of the light path from the light source portion to the sample placement portion so as to not occlude the aperture portion when the cover portion is closed,
wherein the cover portion can be opened so as to access the measurement.

* * * * *